United States Patent [19]

Dotolo

[11] 4,379,168
[45] Apr. 5, 1983

[54] PESTICIDES CONTAINING D-LIMONENE

[76] Inventor: Vincent Dotolo, 1989 Bellair Rd., Clearwater, Fla. 33516

[21] Appl. No.: 295,448

[22] Filed: Aug. 24, 1981

Related U.S. Application Data

[63] Continuation of Ser. No. 130,138, Mar. 14, 1980, abandoned.

[51] Int. Cl.³ .............................................. A01N 27/00
[52] U.S. Cl. ..................................................... 424/356
[58] Field of Search ......................................... 424/356

[56] References Cited

PUBLICATIONS

Chem. Abst. 70, 35483(g), (1969)–Smelyanets et al., Toxicity of Some Terpene Compounds.
Chem. Abst. 76, 42769(g), (1972)–Rudnell et al.
Chem. Abst. 88, 116302(w), (1978)–Oshkaev et al., Toxic Effects of Monoterpenes.
Chem. Abst. 90, 17691(g), (1979)–Tsuigaito et al., Insecticide Aerosol Composition Contain Limonene.

Primary Examiner—Douglas W. Robinson
Attorney, Agent, or Firm—James C. Wray; Craig B. Bailey

[57] ABSTRACT

Pesticide compositions are disclosed which contain D-limonene as an insect-killing ingredient along with surfactants or emulsifiers and water. The pesticide compositions are liquids designed for use as a flexible-purpose pesticide concentrate; a dip to rid small animals of fleas and ticks; a spray to kill fleas and ticks on small animals and in the kennels of small animals; a spray to kill flies on small animals and in the kennels of small animals; and a spray or liquid to rid household areas of cockroaches and other insect pests. The composition is non-toxic, non-polluting, biodegradable, non-irritating to animals other than insect pests.

37 Claims, No Drawings

PESTICIDES CONTAINING D-LIMONENE

This application is a continuation of Ser. No. 130,138, filed Mar. 14, 1980, now abandoned.

BACKGROUND OF THE INVENTION

This invention relates to pesticide compositions containing D-limonene which are useful for killing insect pests on small animals, in the kennels of small animals and in household areas which attract insect pests.

D-limonene is a water white to slightly yellow monocyclic terpene obtained as a byproduct of the manufacture of citrus molasses. It is obtained by steam distillation of citrus peels and pulp resulting from the production of citrus juices and is referred to as a "stripper oil," which contains about 94–98% of the D-limonene.

BRIEF DESCRIPTION OF THE INVENTION

It is the object of this invention to provide pesticide compositions comprising D-limonene.

It is another object of this invention to provide a pesticide composition comprising D-limonene for topical application on small animals, i.e., an animal pesticide dip.

It is a further object of this invention to provide a pesticide composition comprising D-limonene as a flexible-purpose concentrate to be diluted with water for use.

It is an additional object of this invention to provide a pesticide composition containing D-limonene which is suitable for spraying on small animals or in the kennels of small animals to kill fleas and ticks.

Another object of this invention is to provide a pesticide composition containing D-limonene which is suitable for spraying on small animals or in the kennels of small animals to kill flies.

An additional object of this invention is to provide a pesticide composition containing D-limonene which is suitable for use in ridding household areas of cockroaches and other insect pests.

DETAILED DESCRIPTION OF THE INVENTION

The invention is particularly concerned with the provision of various pesticide compositions containing as their principal ingredient D-limonene. These compositions are suitable for use on small animals, in the kennels of such animals and on household surfaces which attract insect pests. The D-limonene is used as a pesticide along with surfactants or emulsifiers and water.

Any suitable surface-active agents, i.e., emulsifiers and surfactants, can be used in the pesticide compositions which serve to emulsify the D-limonene. A surfactant particularly suitable is octylphenox polyethoxy ethanol, which is commercially available from the Rohm and Haas Company under the tradename, TRITON X-100. This surfactant is stated to contain 10 moles of ethylene oxide per molecule and to have a viscosity of 250 centipoises at 77° F. (Brookfield) and a specific gravity of about 1.065 at 77° F. A suitable emulsifier which can be used is commercially available from the Stepan Chemical Company under the tradename, WHC. It is an equilibrium mixture comprising 20–40% mixed soap, 10–20% polyhydric alcohol and 5–15% mixed fatty acids. Another suitable surfactant which can be used is commercially available from the GAF Corporation under the tradename, IGEPAL CO-630. It is a nonylphenoxypoly (ethyleneoxy) ethanol with 65% ethylene oxide and a molar ratio, i.e., the number of moles of ethylene oxide per mole of nonylphenol, of 9.

Although the above specific surfactants and emulsifiers have been set forth, it is understood that any suitable surfactant or emulsifier can be used. Such a surfactant or emulsifier can be of the non ionic anionic, cationic or amphoteric type and can be of natural or synthetic origin, providing that it is in liquid form as used herein and serves to emulsify with the D-limonene.

The various components of the pesticide compositions are to be used in various proportions depending on the use to be made of the specific pesticide composition. When used as a pesticide for topical application on small animals, i.e., an animal pesticide dip, the composition comprises about 2–25% D-limonene, about 1–15% surfactant or emulsifier and the remainder water by volume. Typically, the composition comprises about 2–10% D-limonene, about 1–7% surfactant or emulsifier and the remainder water by volume. A preferable composition comprises about 4–7% D-limonene, about 3.5–4.5% surfactant or emulsifier and the remainder water by volume.

When used as a sprayed, flea-and-tick-killing agent on small animals and in their kennels, the composition comprises about 1–12% D-limonene, about 0.5–10% surfactant or emulsifier and the remainder water by volume. Typically, the composition comprises about 1–6% D-limonene, about 0.5–5% surfactant or emulsifier and the remainder water by volume. A preferable composition comprises about 4–5% D-limonene, about 2–4% surfactant or emulsifier and the remainder water by volume.

When used as a sprayed, fly-killing agent on small animals and in their kennels, the composition comprises about 3–30% D-limonene, about 2–10% surfactant or emulsifier and the remainder water by volume. Typically, the composition comprises about 3–8% D-limonene, about 2–6% surfactant or emulsifier and the remainder water by volume. A preferable composition comprises about 4–7% D-limonene, about 3.5–4.5% surfactant or emulsifier and the remainder water by volume.

When used as an agent to kill cockroaches and other insect pests on household surfaces, the composition comprises about 2–25% D-limonene, about 1–15% surfactant or emulsifier and the remainder water by volume. Typically, the composition comprises about 2–10% D-limonene, about 1–7% surfactant or emulsifier and the remainder water by volume. A preferable composition comprises about 4–7% D-limonene, about 3.5–4.5% surfactant or emulsifier and the remainder water by volume.

The following examples are set forth to further illustrate the present invention but are not intended to be limiting in any sense. The proportions of components are set forth in volume percentages.

EXAMPLE 1

ANIMAL PESTICIDE DIP

Emulsifer WHC: 0.5
D-limonene: 3% oil
Water: remainder

EXAMPLE 2

ANIMAL PESTICIDE DIP

Emulsifier DOW 555: 5%

D-limonene: 30% oil
Water: remainder

EXAMPLE 3
ANIMAL PESTICIDE DIP

Emulsifier TRITON X-100: 0.005%
D-limonene: 0.03%
Water: remainder

When using one of these compositions as a dip for small animals, there is no need to rinse the composition off. It leaves a pleasant, citrus scent and continues to exhibit effectiveness as a pesticide after it has been applied. Because the animal pesticide dip has cleaning properties as well, it can also be used for bathing small animals.

EXAMPLE 4
ANIMAL PESTICIDE DIP

Emulsifier WHC: 0.7%
IGEPAL CO-630: 0.3%
D-limonene: 6%
Water: remainder

EXAMPLE 5
ANIMAL PESTICIDE DIP

Emulsifier DOW 555: 7%
IGEPAL CO-630: 3%
D-limonene: 60%
Water: remainder

EXAMPLE 6
ANIMAL PESTICIDE DIP

Emulsifier TRITON X-100: 0.007%
IGEPAL CO-630: 0.003%
D-limonene: 0.06%
Water: remainder Examples 4-6 are compositions which can be used when residual properties are either not required or desired.

EXAMPLE 7
FLEA AND TICK SPRAY

Emulsifier WHC: 0.36%
D-limonene: 2.2%
Water: remainder

EXAMPLE 8
FLEA AND TICK SPRAY

Emulsifier DOW 555: 3.6%
D-limonene: 22%
Water: remainder

EXAMPLE 9
FLEA AND TICK SPRAY

Emulsifier TRITON X-100: 0.004%
D-limonene: 0.02%
Water: remainder

The flea and tick spray is effective in ridding the kennels of small animals of fleas and ticks. Because it is non-irritating, it can be sprayed directly on animals, as well.

EXAMPLE 10
FLEA AND TICK SPRAY

Emulsifier WHC: 0.54%
IGEPAL CO-630: 0.18%
D-limonene: 4.5%
Water: remainder

EXAMPLE 11
FLEA AND TICK SPRAY

Emulsifier DOW 555: 5.4%
IGEPAL CO-630: 1.8%
D-limonene: 45%
Water: remainder

EXAMPLE 12
FLEA AND TICK SPRAY

Emulsifier TRITON X-100: 0.005%
IGEPAL CO-630: 0.002%
D-limonene: 0.045%
Water: remainder Examples 10-12 are compositions which can be used when residual properties are either not required or desired.

EXAMPLE 13
FLY SPRAY

Emulsifier WHC: 0.4%
D-limonene: 2%
Water: remainder

EXAMPLE 14
FLY SPRAY

Emulsifier DOW 555: 4%
D-limonene: 20%
Water: remainder

EXAMPLE 15
FLY SPRAY

Emulsifier TRITON X-100: 0.004%
D-limonene: 0.02%
Water: remainder

The fly spray is effective in ridding the kennels of small animals of flies. Its residual effect provides the added benefit of killing flies after the spray has settled onto kennel surfaces.

EXAMPLE 16
FLY SPRAY

Emulsifier WHC: 0.5%
IGEPAL CO-630: 0.2%
D-limonene: 5.0%
Water: remainder

EXAMPLE 17
FLY SPRAY

Emulsifier DOW 555: 5%
IGEPAL CO-630: 2%
D-limonene: 50%
Water: remainder

EXAMPLE 18
FLY SPRAY

Emulsifier TRITON X-100: 0.005%

IGEPAL CO-630: 0.002%
D-limonene: 0.05%
Water: remainder

Examples 16–18 are compositions which can be used when residual properties are either not required or desired.

EXAMPLE 19
FLEXIBLE USE PESTICIDE CONCENTRATE

Emulsifier WHC: 6%
IGEPAL CO-630: 2%
D-limonene: 50%
Water: remainder

EXAMPLE 20
FLEXIBLE USE PESTICIDE CONCENTRATE-(Gel)

Emulsifier DOW 555: 15%
IGEPAL CO-630: 6%
D-limonene: 60%
Water: remainder

EXAMPLE 21
FLEXIBLE USE PESTICIDE CONCENTRATE

Emulsifier TRITON X-100: 0.6%
IGEPAL CO-630: 0.2%
D-limomene: 50%
Water: remainder By diluting the concentrate with water in varying amounts, the user can adapt the composition to meet a wide variety of pesticide needs, both safely and effectively.

EXAMPLE 22
FLEXIBLE USE PESTICIDE CONCENTRATE

Emulsifier WHC: 8%
D-limonene: 50%
Water: remainder

EXAMPLE 23
FLEXIBLE USE PESTICIDE CONCENTRATE

Emulsifier DOW 555: 0.8%
D-limonene: 5%
Water: remainder

EXAMPLE 24
FLEXIBLE USE PESTICIDE CONCENTRATE

Emuslifier TRITON X-100: 20%
D-limonene: 60%
Water: remainder

The concentrate, which can be put to a wide variety of uses when diluted, offers the added benefit of residual effectiveness.

EXAMPLE 25
HOUSEHOLD PESTICIDE

Emulsifier TRITON X-100: 0.5%
D-limonene: 3%
Water: remainder

EXAMPLE 26
HOUSEHOLD PESTICIDE

Emulsifier WHC: 5%
D-limonene: 30%
Water: remainder

EXAMPLE 27
HOUSEHOLD PESTICIDE

Emulsifier DOW 555: 0.005%
D-limonene: 0.03%
Water: remainder

The household pesticide is effective in killing cockroaches, as well as flies. It can be sprayed or applied directly on household surfaces which attract such insect pests.

EXAMPLE 28
HOUSEHOLD PESTICIDE

Emulsifier WHC: 0.7%
IGEPAL CO-630: 0.3%
D-limonene: 6%
Water: remainder

EXAMPLE 29
HOUSEHOLD PESTICIDE

Emulsifier TRITON X-100: 7%
IGEPAL CO-630: 3%
D-limonene: 60%
water: remainder

EXAMPLE 30
HOUSEHOLD PESTICIDE

Emulsifier DOW 555: 0.007%
IGEPAL CO-630: 0.003%
D-limonene: 0.06%
Water: remainder Examples 28–30 are compositions which can be used when residual properties are either not required or desired.

The above pesticide compositions are biodegradable, non-polluting and non-irritating to the skin.

The D-limonene in them should contain a suitable, commercially available preservative, such as BHT, to retain its original state and prevents its becoming rancid.

The Shell Company markets a suitable preservative under the tradename, IONOL.

The D-limonene should also contain a bacteriostat. The Lonza Company markets a suitable bacteriostat under the tradename, BARDAC 22.

Although the examples set forth generally relate to pesticide uses in houses, kennels or on the bodies of such small animals as dogs, cats and other household pets, compositions D-limonene offer active and residual pesticide protection for livestock, as well. When treated with these compositions, cattle, dairy herds, sheep, horses and other domestic animals can be rid of flies, fleas, ticks and other insect pests.

After animals are brushed with compositions leaving a residue of D-limonene and surfactant, the sheen of their coats is also enhanced.

In such instances, the pesticides compositions can be used in spray form, in liquid form or in the form of a "wipe" or saturated pad made of cotton or any other suitable absorbent material, which can be rubbed into the coats of the animals.

When made by the proper volumetric combination of oil, surfactant and water, the compositions can also be used in the form of a gel, which can be squeezed from a tube onto the hands and applied from the hands onto the coats of animals.

In addition, compositions containing D-limonene are effective in ridding chickens of lice.

When applied to walls or floors, compositions containing D-limenene and surfactant which leave a residue are also effective as cleaners offering the important additional benefit of helping to protect houses, kennels and other animal quarters from common insect pests.

In all products and especially in the concentrate it is desirable to use deionized water.

In all products there may be used a single surfactant or a two surfactant system. The single surfactant is preferred when it is desired to leave a film of the D-Limonene and the surfactant. The film may continue on the pesticide effect which may be active while water is evaporating and after evaporation is complete. The two surfactant system is used when it is desired to completely remove the product by rinsing away all traces and films with clear water. It is believed that the second surfactant helps soluabilize and emulsify the film forming combination of the first surfactant and the oil.

The contrate may be in the form of a liquid or gel, preferably it is a liquid for ease in dissolution in water. It is preferred to dilute the concentrate by adding the desired amount of concentrate into the desired amount of water while stirring the water. Heating the water is unnecessary, but is may speed the forming of a uniform emulsion when the concentrate is a gel.

The concentrate may be entirely D-limonene and surfactant, preferably the concentrate includes water. In both cases, the concentrate is preferably a liquid.

When a concentration of surfactant exceeds about 15% and oil exceeds about 60% with the balance water, a gel results. The gel is suitable as a topical pesticide. A quantity may be spread over the hands or on a cloth and rubbed over the fur or hide of an animal. The application destroys pests and leaves a residual film to repell and kill insects. When a single or two surfactant system is used, wetting the animal may improve the result. When the two surfactant system is used, the animal may be rinsed free of the material using clear water.

The preferred contration of the concentrate provides a stable long shelf life composition with trouble free mixing capabilities and easy and safe handling and clean up.

The contrate and all its derivative products are non-toxic, non-irritants, non-pollutants and are biodegradeable.

The preferred formulations of the concentrate and the products are as follows:

|  | Parts by Volume | | | |
| --- | --- | --- | --- | --- |
|  | range | preferred | range | preferred |
|  | Concentrate 1 | | Concentrate 2 | |
| D-limonene | 100 | 100 | 100 | 100 |
| Deionized water | 0–300+ | 84 | 0–300 | 84 |
| Surfactant WHC | 2–30 | 16 | 2–30 | 12 |
| Surfactant Igepal |  |  | 1–24 | 4 |
| Anti Oxidant | 10–100 | 25 | 10–100 | 35 |
| Bacteriostat | .001–.1 | 01 | .001–.1 | .01 |
|  | Concentrate Strengths (%) | | | |
| Products | .05–50 | 4.5 | 1–60 | 9 |
| Spray | .05–50 | 4.5 | 1–60 | 9 |
| Dip | .05–60 | 6 | 1–60 | 12 |
| Pesticidal Cleaner (Wall) | 2–50 | 16 | 2–50 | 16 |
| Pesticidal Cleaner (Floor) | 2–50 | 3 | 2–50 | 3 |

Throughout the specification and claims "surfactant" is used to include one or more specific surfactants unless otherwise indicated and is used generically to include emulsifiers.

While the exact operation of the pesticide is not known, it is believed that the D-limonene surfactant and water emulsion forms a fine film completely coating insects.

Cold water solutions are effective. Hot water solutions aid the vaporization of the components making the product more effective and quicker.

In addition, the vapors of the components and the penetrating characteristics of the film suffocate and destroy the insects. It is believed that the mass of the pesticide and film compared to the mass of the insect is such that the penetrating and rebuilding film overwhelms the insects and renders them and their biosystems non-functional.

While the invention has been described with reference to specific embodiments, examples, products and ranges, it will be obvious to those skilled in the art that modification may be made without departing from the invention, which is specifically pointed out in the following claims.

What is claimed is:

1. A pesticide composition for topical application on small animals, i.e., an animal pesticide dip consisting essentially of about 2–25% D-limonene from citrus products about 1–15% liquid, water soluble, surface-active agent capable of emulsifying the D-limonene, and the remainder water, by volume.

2. The pesticide composition of claim 1 wherein said D-limonene is present at about 2–10% by volume and said surface-active agent is present at about 1–7% by volume.

3. The pesticide composition of claim 1 wherein the D-limonene is present at about 4–7% by volume and the surface-active agent is present at about 3.5–4.5% by volume.

4. The pesticide composition of claim 1 wherein the surface-active agent is selected from the group consisting of an octylphenoxy polyethoxy ethanol surfactant containing about 10 moles of ethylene oxide per molecule, and a surfactant consisting of a mixture of nonylphenoxypoly(ethyleneoxy) ethanol and ethylene oxide in a molar ratio of about 1:9.

5. The pesticide composition of claim 1 wherein the surface-active agent consists of an octylphenoxy polyethoxy ethanol surfactant containing about 10 moles of ethylene oxide per molecule.

6. The pesticide composition of claim 1 wherein the surface-active agent is a surfactant consisting of a mixture of nonylphenoxypoly (ethyleneoxy) ethanol and ethylene oxide in a molar ratio of about 1:9.

7. A flea-and-tick-killing composition for spray use on small animals and in their kennels consisting essentially of about 1–12% D-limonene from citrus products, about 0.5–10% liquid, water soluble, surface-active agent capable of emulsifying the D-limonene, and the remainder water, by volume.

8. The flea-and-tick-killing composition of claim 7 wherein said D-limonene is present at about 1–6% by volume and said surface-active agent is present at about 0.5–5% by volume.

9. The flea-and-tick-killing composition of claim 7 wherein the surface-active agent is present at about 2–4% by volume and the D-limonene is present at about 4–5% by volume.

10. The flea-and-tick-killing composition of claim 7 wherein the surface-active agent is selected from a group consisting of an octylphenoxy polyethoxy enthanol surfactant containing about 10 moles of ethylene oxide per molecule, and a surfactant consisting of a mixture of nonylphenoxypoly (ethyleneoxy) ethanol and ethylene oxide in a molar ratio of about 1:9.

11. The flea-and-tick-killing composition of claim 7 wherein the surface-active agent consists of an octylphenoxy polyethoxy ethanol surfactant containing about 10 moles of ethylene oxide per molecule.

12. The flea-and-tick-killing composition of claim 7 wherein the surface-active agent is a surfactant consisting of a mixture of nonylphenoxypoly (ethyleneoxy) ethanol and ethylene oxide in a molar ratio of about 1:9.

13. A fly-killing composition for spray use on small animals and in the kennels of small animals consisting essentially of about 3—30% D-limonene from citrus products about 2–10% liquid, water soluble, surface-active agent capable of emulsifying the D-limonene, and the remainder water, by volume.

14. The fly-killing composition of claim 13 wherein said D-limonene is present at about 3–8% by volume and said surface-active agent is present at about 2–6% by volume.

15. The fly-killing composition of claim 13 wherein the surface-active agent is present at about 3.5–4.5% by volume and the D-limonene is present at about 4–7% by volume.

16. The fly-killing composition of claim 13 wherein the surface-active agent is selected from the group consisting of an octylphenoxy polyethoxy ethanol surfactant containing about 10 moles of ethylene oxide per molecule, and a surfactant consisting of a mixture of nonylphenoxypoly (ethyleneoxy) ethanol and ethylene oxide in a molar ratio of about 1:9.

17. The fly-killing composition of claim 13 wherein the surface-active agent consists of an octylphenoxy polyethoxy ethanol surfactant containing about 10 moles of ethylene oxide per molecule.

18. The fly-killing composition of claim 17 wherein the surface-active agent is a surfactant consisting of a mixture of nonylphenoxypoly (ethyleneoxy) ethanol and ethylene oxide in a molar ratio of about 1:9.

19. A concentrated pesticide composition for flexible topical use on animals following dilution with water, consisting essentially of about 0.5–60% D-limonene from citrus products, about 0.8–21% liquid, water soluble surface-active agent capable of emulsifying the D-limonene and the remainder water, by volume.

20. The pesticide composition of claim 19 wherein the surface-active agent is present at about 8% by volume and the D-limonene is present at about 50% by volume.

21. The pesticide composition of claim 19 wherein the surface-active agent is selected from the group consisting of an octylphenoxy polyethoxy ethanol surfactant containing about 10 moles of ethylene oxide per molecule, and a surfactant consisting of a mixture of nonylphenoxypoly (ethyleneoxy) ethanol and ethylene oxide in a molar ratio of about 1:9.

22. The pesticide composition of claim 19 wherein the surface-active agent consists of an octylphenoxy polyethoxy ethanol surfactant containing about 10 moles of ethylene oxide per molecule.

23. The pesticide composition of claim 19 wherein the surface-active agent is a surfactant consisting of a mixture of nonylphenoxypoly (ethyleneoxy) ethanol and ethylene oxide in a molar ratio of about 1:9.

24. The pesticide composition of claim 1 wherein the D-limonene and the surface-active agent are present in a volume ratio of about 6:1.

25. The pesticide composition of claim 24 wherein the surface-active agent consists of a mixture of two surface-active agents in a volume ratio of about 7:3.

26. The flea-and-tick-killing composition of claim 7 wherein the D-limonene and the surface-active agent are present in a volume ratio of about 6:1.

27. The flea-and-tock-killing composition of claim 26 wherein the surface-active agent consists of a mixture of two surface-active agents in a volume ratio of about 3:1.

28. The fly-killing composition of claim 13 wherein the D-limonene and the surface-active agent are present in a volume ratio of about 5:1.

29. The fly-killing composition of claim 28 wherein the surface-active agent consists of a mixture of two surface-active agents in a volume ratio of about 5:2.

30. The concentrated pesticide composition of claim 19 wherein the D-limonene and surface-active agent are present in a volume ratio of about 6:1.

31. The concentrated pesticide composition of claim 19 wherein the D-limonene and surface-active agent are present in a volume ratio of about 3:1.

32. The pesticide of claim 30 wherein the surface-active agent consists of a mixture of two surface-active agents in a volume ratio of about 3:1.

33. The pesticide of claim 31 wherein the surface-active agent consists of a mixture of two surface-active agents in a volume ratio of about 5:2.

34. A method for protecting animals against pests comprising
distilling citrus products to obtain a by-product which includes D-limonene,
mixing about 2–25% by volume of said D-limonene with water and with about 1–15% by volume of a water soluble, surface-active agent capable of emulsifying the D-limonene,
blending the resultant composition to obtain a pesticide, and
applying the pesticide to the coat and skin of an animal.

35. The method of claim 34 comprising mixing about 1–12% by volume D-limonene, about 0.5–10% by volume surface-active agent, and the remainder water, said composition being useful as a flea-and-tick-killing composition.

36. The method of claim 34 comprising mixing about 3–25% by volume D-limonene, about 2–10% by volume surface-active agent, and the remainder water, said composition being useful as a fly-killing composition.

37. The method of claim 34 wherein the distilling step comprises steam distilling citrus peels and pulp.

* * * * *

REEXAMINATION CERTIFICATE (1194th)

United States Patent [19]

Dotolo

[11] B1 4,379,168

[45] Certificate Issued  Jan. 23, 1990

[54] PESTICIDES CONTAINING D-LIMONENE

[76] Inventor: Vincent Dotolo

Reexamination Request:
No. 90/000,387, May 27, 1983

Reexamination Certificate for:
Patent No.: 4,379,168
Issued: Aug. 24, 1981
Appl. No.: 295,448
Filed: Apr. 5, 1983

Related U.S. Application Data

[63] Continuation of Ser. No. 130,318, Mar. 14, 1980, abandoned.

[51] Int. Cl.⁴ .............................................. A01N 27/00
[52] U.S. Cl. .................................................... 514/763

[56] References Cited

U.S. PATENT DOCUMENTS

Re. 29,649  0/1978  Farnsworth .
3,023,144   0/1962  Greathouse .

FOREIGN PATENT DOCUMENTS 54-14406 of 1979 Japan .

OTHER PUBLICATIONS

Taylor, W. E. et al., "Insecticidal Properties of Limonene, a Constituent of Citrus Oil", *Ghana Journal of Agricultural Science*, 7(1) 61–62 (1974).

Smelyanets, V. P. et al, "Toxicity of Some Terpene Compounds", *Khim. Sel. Khoz.*, 1968, 6 (10), 754–4.
Chemical Abstracts, 70:35483g (1969)–Smelyanets et al, "Toxicity of some terpene compounds".
Chemical Abstracts, 76:42769g (1972)–Rudnew et al, "Causes of Rapid Reproduction in Some Woodland Pests".
Chemical Abstracts 88:116302w (1978)–Oshkaev et al, "Toxic Effects on Monoterpenes on Conifer-Needle–Chewing [insects] and Cone and Seed Pests".
Chemical Abstracts 90:17691g (1979)–Tsujigaito et al, "Insecticide Aerosol Composition Containing Limonene".
Coleman, R. L., "D–Limonene as a Degreasing Agent", *The Citrus Industry*, vol. 56, pp. 23–25, Nov. 1975.
Valdhuis, M. K., "Distilled Oils Could Become Important Profit Item", *Citrus World*, 4:12, 23 (1968).

*Primary Examiner*—Douglas W. Robinson

[57] ABSTRACT

Pesticide compositions are disclosed which contain D-limonene as an insect-killing ingredient along with surfactants or emulsifiers and water. The pesticide compositions are liquids designed for use as a flexible-purpose pesticide concentrate; a dip to rid small animals of fleas and ticks; a spray to kill fleas and ticks on small animals and in the kennels of small animals; a spray to kill flies on small animals and in the kennels of small animals; and a spray or liquid to rid household areas of cockroaches and other insect pests. The composition is non-toxic, non-polluting, biodegradable, non-irritating to animals other than insect pests.

REEXAMINATION CERTIFICATE ISSUED UNDER 35 U.S.C. 307

THE PATENT IS HEREBY AMENDED AS INDICATED BELOW.

Matter enclosed in heavy brackets [] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 1, lines 2-3:
This application is a continuation of Ser. No. 130,138, filed Mar. 14, 1980, now abandoned; *continuation-in-part of Ser. No. 090,238, Nov. 1, 1979, abandoned; continuation of Ser. No. 812,688, July 5, 1977, abandoned.*

AS A RESULT OF REEXAMINATION, IT HAS BEEN DETERMINED THAT:

Claims 1-37 are cancelled.

* * * * *